United States Patent [19]

Lüthi et al.

[11] 4,003,875
[45] Jan. 18, 1977

[54] ASYMMETRICAL OXALIC ACID DIARYL AMIDE STABILIZERS

[75] Inventors: Christian Lüthi, Basel; Max Dünnenberger, Frenkendorf; Hans Rudolf Biland, Gelterkinden, all of Switzerland

[73] Assignee: Ciba-Geigy Corporation, Ardsley, N.Y.

[22] Filed: Nov. 19, 1975

[21] Appl. No.: 633,200

Related U.S. Application Data

[63] Continuation-in-part of Ser. No. 376,665, July 5, 1973, abandoned, which is a continuation-in-part of Ser. No. 253,070, May 15, 1972, abandoned, which is a continuation of Ser. No. 820,712, April 29, 1969, abandoned, which is a continuation-in-part of Ser. No. 614,039, Feb. 6, 1967, Pat. No. 3,529,982.

[30] Foreign Application Priority Data

Feb. 7, 1966 Switzerland .................... 1.680/66

[52] U.S. Cl. ................ 260/45.9 NC; 260/398.5; 106/178
[51] Int. Cl.² .......................................... C08K 5/25
[58] Field of Search ............... 260/45.9 NC, 398.5; 106/178

[56] References Cited

UNITED STATES PATENTS

| 3,808,273 | 4/1974 | Burdet et al. ............ 760/45.9 NC |
| 3,904,582 | 9/1975 | Hansen ..................... 760/45.9 NC |
| 3,906,033 | 9/1975 | Biland et al. ............. 760/45.9 NC |
| 3,906,041 | 9/1975 | Hofer et al. .............. 260/45.9 NC |

*Primary Examiner*—V. P. Hoke
*Attorney, Agent, or Firm*—Luther A. R. Hall

[57] ABSTRACT

The invention concerns specific new oxalic acid diarylamides which are characterized by an asymmetrical substitution with regard to the central oxalic amide moiety of the formula

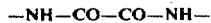

—NH—CO—CO—NH— and by substitution with one or two alkoxy, alkenyloxy, aralkenyloxy or acyloxy groups. Definite additional substituents may be present. The compounds are valuable ultraviolet stabilizers.

12 Claims, No Drawings

ASYMMETRICAL OXALIC ACID DIARYL AMIDE STABILIZERS

This is a continuation-in-part of Ser. No. 376,665 now abandoned, filed July 5, 1973, which in turn is a continuation-in-part of Ser. No. 253,070, filed May 15, 1972, now abandoned, which in turn was a continuation application Ser. No. 820,712, filed Apr. 29, 1969, now abandoned, which in turn was a continuation-in-part of Ser. No. 614,039, filed Feb. 6, 1967, now U.S. Pat. No. 3,529,982.

The present invention provides asymmetrical oxalic acid diarylamides and processes for their manufacture and use as light filters, especially ultraviolet absorbers, for organic materials that are damaged by the action of ultraviolet rays.

It is known e.g. from U.S. Pat. No. 2,665,265 to use chelate complexes of copper or nickel with aromatic o-hydroxy diazo compounds as ultraviolet stabilizers. These compounds have the disadvantage to be colored, and therefore they are not suitable stabilizers for transparent substrates. Further on it has already been described that oxalic acid bishydroxyl arylamides are suitable for use as ultraviolet absorbers, but in the past it had been held that the light stability of such compounds depends on the presence of two free hydroxyl groups in ortho-position relative to the amide nitrogen atom. In contradistinction to this assumption, it has now been surprisingly found that a large class of asymmetric oxalic acid diarylamides that do not satisfy the requirement referred to, are excellent ultraviolet absorbing agents suitable for industrial use.

The new asymmetrical oxalic acid diarylamides of this invention relates to the formula

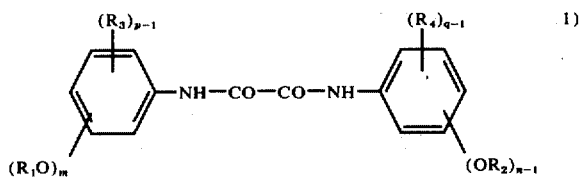

in which $R_1$ and $R_2$ each represents an alkyl group with 1 to 18 carbon atoms which may be substituted by chlorine, hydroxyl groups, alkoxy groups with 1 to 4 carbon atoms, carboxyl groups, nitrile groups, carboxylic acid amide groups or carboxylic acid alkyl ester groups with 1 to 12 carbon atoms; an alkenyl group containing 3 or 4 carbon atoms; a benzyl group which may be substituted by chlorine or alkyl; an aliphatic acyl group with up to 18 carbon atoms; a benzoyl group which may be substituted by chlorine or an alkyl group with 1 to 4 carbon atoms; $R_3$ and $R_4$ each represents an alkyl group with 1 to 12 carbon atoms, a halogen atom, a halogenalkyl group, a sulphonic acid group, a phenyl group or a phenylalkyl group whose alkyl residue contains 1 to 4 carbon atoms, or two ortho-positioned residues $R_3$ and/or $R_4$ together form a fused-on six-membered aromatic carbon ring, and where $m$ and $n$ = 1 or 2 and $p$ and $q$ = 1, 2 or 3, each of the two ring systems containing in addition to the bond via the -NH- group at most 3 substituents and the sum $m+(n-1)$ being 1 or 2, and in other respects the substituents $R_1O-$, $R_2O-$, $R_3$ and $R_4$ being of a type, number and in positions such that the molecule is asymmetrical. In this formula and in the following formulae the index symbols $m$, $n$, $p$ and $q$ (and $r$, $s$, $t$ and $u$ respectively) are to be interpreted so that, if the symbol stands for O, a hydrogen atom in each case takes the place of the indicated residue. The term "aliphatic acyl group containing up to 18 carbon atoms" refers both to saturated and unsaturated acyl groups, thus, for example, the acryl group.

Of great value within the scope of the above formula are the compounds of the formula

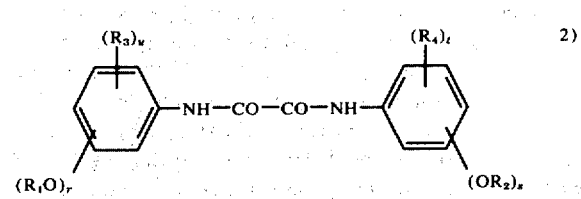

in which $R_1$ and $R_2$ each represents an alkyl group with 1 to 18 carbon atoms which may be substituted by chlorine, hydroxyl groups, alkoxy groups with 1 to 4 carbon atoms, carboxyl groups, carboxylic acid amide groups or carboxylic acid alkyl ester groups with 1 to 12 carbon atoms; an alkenyl group with 3 or 4 carbon atoms; a benzyl group which may be substituted by chlorine and methyl groups; an aliphatic acyl group containing up to 18 carbon atoms; a benzoyl group which may be substituted by chlorine or an alkyl group with 1 to 4 carbon atoms; $R_3$ and $R_4$ each represents an alkyl group with 1 to 12 carbon atoms, a halogen atom, a halogenalkyl group, a sulphonic acid group, a phenyl group or a phenylalkyl group whose alkyl residue contains 1 to 4 carbon atoms or two ortho-positioned residues $R_3$ and/or $R_4$ together form a fused-on six-membered aromatic carbon ring and $r$, $s$, $t$ and $u$ each = 0 or 1, and the sum $(r+s) = 1$ or 2.

Of special value are new asymmetrical oxalic acid diarylamides of the formula

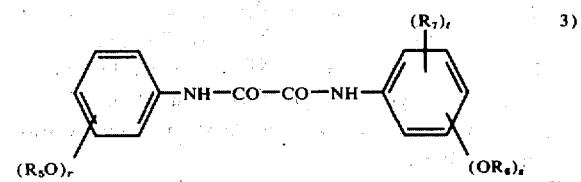

in which $R_5$ and $R_6$ each represents an alkyl group with 1 to 18 carbon atoms which may be substituted by chlorine atoms, hydroxyl groups or alkoxy groups with 1 to 4 carbon atoms, an alkyl group, a benzyl group which may be substituted by chlorine or methyl groups, a carbomethoxy- or carbethoxy-alkyl group with 1 to 6 carbon atoms in the alkyl grouping, an aliphatic acyl group with 1 to 12 carbon atoms, or a benzoyl group which may be substituted by chlorine or an alkyl group with 1 to 4 carbon atoms; $R_7$ represents an alkyl group with 1 to 18 carbon atoms, chlorine or a phenyl group, and $r$, $s$ and $t = 0$ or 1 and the sum $(r+s) = 1$ or 2, and in other respects the substituents $R_5O-$, $R_6O-$ and $R_7$ differ from each other as to type, number and positions so that the molecule is asymmetrical.

As further types of compounds of outstanding practical value there may be mentioned the following: (a) Compounds of the formula

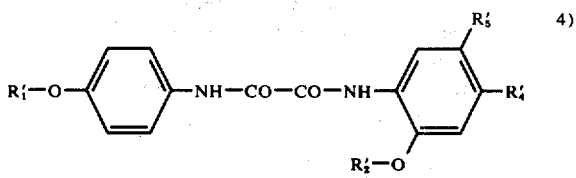

in which $R_1'$ represents an alkyl group with 1 to 4 carbon atoms, $R_2'$ an alkyl group with 1 to 18 carbon atoms, an alkyl group with 1 to 8 carbon atoms which may be substituted by halogen, an alkoxy group with 1 to 4 carbon atoms, a nitrile, carboxyl, carboxylic acid amide or carboxylic acid ester group containing 1 to 18 carbon atoms, an allyl group, a benzyl group, an aliphatic acyl group with 1 to 12 carbon atoms or a benzoyl radical; $R_4$ represents hydrogen, an alkyl group with 1 to 6 carbon atoms, an alkoxy group with 1 to 4 carbon atoms, a phenyl group or halogen; and $R_5'$ represents hydrogen, a phenyl group, an alkyl group with 1 to 12 carbon atoms or a phenylalkyl group.

Particularly efficacious asymmetrical oxalic acid diarylamides have the formula

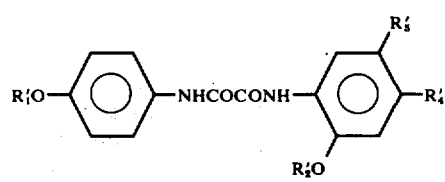

wherein
$R_1'$ is methyl or ethyl,
$R_2'$ is alkyl with 1 to 18 carbon atoms, 3-chloropropyl, 2-chloroethyl, allyl, benzyl, alkanoyl with 2 to 12 carbon atoms, acrylyl, benzoyl, p-chlorobenzoyl, p-tertbutylbenzoyl, 5-cyano-3-oxapentyl, carboethoxymethyl, carboxymethyl, carbododecyloxymethyl, butylcarbamyl or carbaniloylmethyl,
$R_4'$ is hydrogen, methyl, methoxy, phenyl or α,α-dimethylbenzyl, and
$R_5'$ is hydrogen, alkyl with 1 to 8 carbon atoms, chlorine or phenyl, and with the further proviso that when $R_2'$ is methyl or ethyl, $R_4'$ and $R_5'$ cannot both be hydrogen at the same time. (b) Compounds of the formula

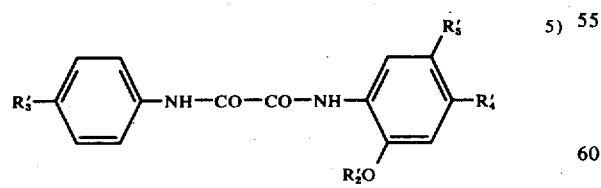

in which $R_3'$ stands for hydrogen, halogen or an alkyl group with 1 to 4 carbon atoms, and $R_2'$, $R_4'$ and $R_5'$ have the same meanings as in formula 4).

Other preferred embodiments of the asymmetrical oxalic acid diarylamides have the formula

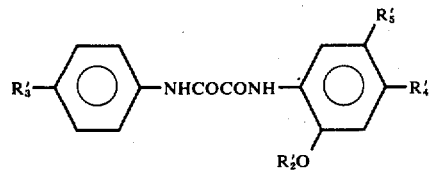

wherein
$R_3'$ is hydrogen, chlorine or methyl,
$R_2'$ is alkyl with 1 to 18 carbon atoms, 3-chloropropyl, carboethoxymethyl, benzyl or acetyl,
$R_4'$ is hydrogen, methoxy or phenyl, and
$R_5'$ is hydrogen or tert-butyl, and with the further proviso that when $R_2'$ is methyl or ethyl, $R_4'$ and $R_5'$ cannot both be hydrogen at the same time. (c) Compounds of the formula

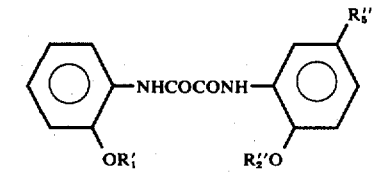

in which $R_1'$ represents an alkyl group with 1 to 4 carbon atoms, $R_2''$ an alkyl group with 1 to 8 carbon atoms, an alkyl group with 1 to 4 carbon atoms which contains halogen atoms or carbalkoxy groups, a benzyl group or an aliphatic acyl group with 1 to 6 carbon atoms; and $R_5''$ stands for hydrogen, halogen or an alkyl group with 1 to 4 carbon atoms.

Other asymmetrical oxalic acid diarylamides exhibiting preferred stabilization activity have the formula

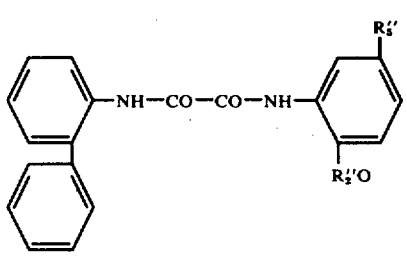

wherein
$R_1'$ is methyl or ethyl,
$R_2''$ is alkyl of 1 to 8 carbon atoms, 3-chloropropyl, benzyl, carboethoxymethyl or acetyl, and
$R_5''$ is hydrogen, chlorine or tert-butyl, and with the further proviso that $R_5''$ cannot be hydrogen when $R_2''$ is methyl or ethyl. (c) Compounds of the formula 6).

where $R_2''$ and $R_5''$ have the same meanings as in formula 6.

Another preferred embodiment of this invention embraces compounds of the formula

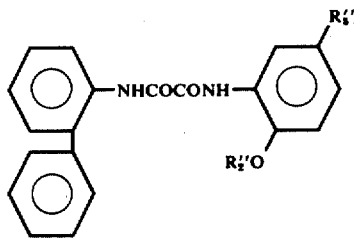

wherein
$R_2''$ is alkyl with 1 to 8 carbon atoms, 3-chloropropyl, carboethoxymethyl or acetyl, and
$R_5''$ is hydrogen or tert-butyl. (e) Compounds of the formula

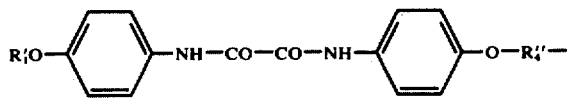

where $R_1'$ stands for an alkyl radical with 1 to 4 carbon atoms and $R_4''$ for an alkyl group with 1 to 12 carbon atoms, an alkenyl group with up to 4 carbon atoms, a benzyl group or an aliphatic or aromatic acyl group with up to 12 carbon atoms.

Another efficacious embodiment of the present invention comprises compound of the formula

wherein
$R_4''$ is alkyl of 4 to 12 carbon atoms, allyl, benzyl, octanoyl, benzoyl or p-tert-butylbenzoyl or butylcarbamyl.

Still another preferred embodiment of the instant invention embraces a compound selected from the group consisting of 2',4'-dimethyl-4''-methoxyoxanilide, 3',5'-dimethyl-4''-methoxyoxanilide, 3,5'-dichloro-4''-methoxyoxanilide 3''-chloro-5'-trifluoromethyl-4''-methoxyoxanilide, 3',5'-ditrifluoromethyl-4''-methoxyoxanilide, N-(4-methoxyphenyl)-N'-(α-naphthyl)oxamide, 2'-methyl-6'-chloro-4''-methoxyoxanilide, 4'-bromo-4''-methoxyoxanilide, 2',2''',5'-triethoxyoxanilide and 4'-cyano-2''-ethoxyoxanilide.

Specifically interesting variants of the compounds of this invention correspond to the following formulae:
Asymmetrical oxalic acid diarylamides of the formula

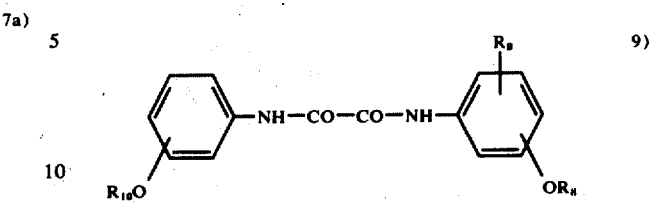

in which $R_8$ represents an alkyl group with 1 to 18 carbon atoms, an alkenyl group with 3 or 4 carbon atoms, an acyl group with 2 to 12 carbon atoms or a benzyl group, $R_9$ may stand for $-O-R_8$ or may stand for a hydrogen or chlorine atom, an alkyl group with up to 12 carbon atoms or a phenyl group, and $R_{10}$ represents an alkyl group with 1 to 4 carbon atoms. Asymmetrical oxalic acid diarylamides of the formula

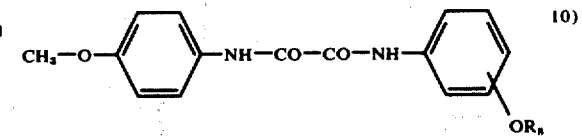

in which $R_8$ stands for an alkyl group with 1 to 18 carbon atoms, an alkenyl group with 3 or 4 carbon atoms, an aryl group with 2 to 12 carbon atoms or a benzyl group.

Asymmetrical oxalic acid diarylamides of the formula

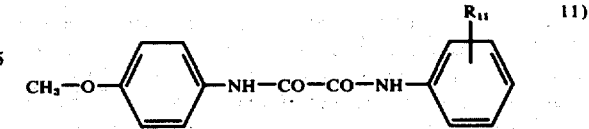

in which $R_{11}$ represents an alkyl group with 1 to 12 carbon atoms, a hydrogen or chlorine atom or a phenyl group.

From the large number of compounds of the above formulae the following compounds may be specially mentioned:

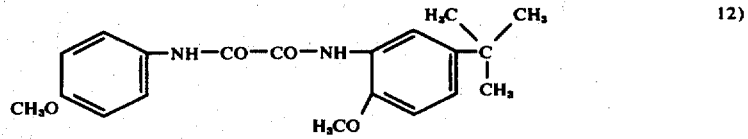

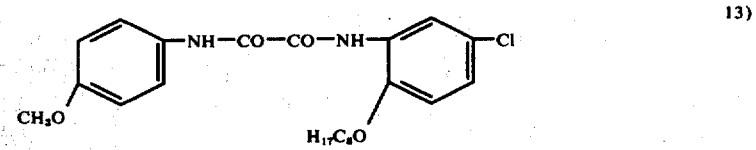

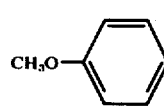
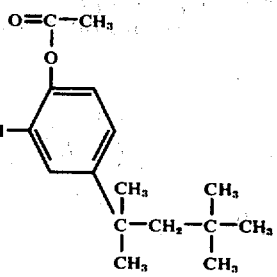

14)

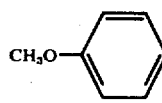
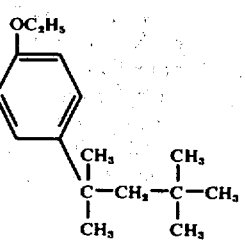

15)

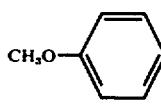
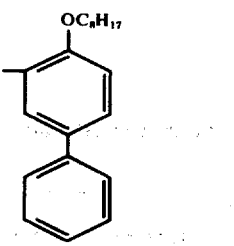

16)

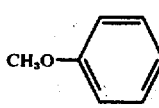
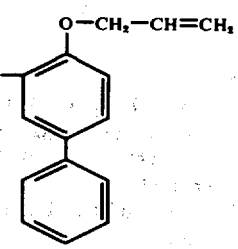

17)

The oxalic acid bis-arylamides of the general formula (1 to be used in this invention are accessible by known methods. They are obtained when oxalic acid or an oxalic acid ester is semi-amidated in known manner in the first stage by reacting oxalic acid or an oxalic acid ester, especially an alkyl ester, with an approximately equimolecular quantity of a corresponding primary amine. According to a preferred method, for example, oxalic acid, an oxalic acid semi-ester or oxalic acid diester containing identical or different ester residues, is condensed with approximately equimolecular quantities of one of the afore-mentioned amines in the melt or in an organic solvent that is inert towards the reactants, in the presence of anhydrous boric acid, at a temperature ranging from about 50° to 200° C.

The resulting amide-ester or amide-acid is isolated and then in a second stage the remaining carboxyl group or carboxylate group respectively of the oxalic acid semi-amide is condensed under analogous conditions with a second amine, for which second condensation it is in general advantageous to use a temperature higher by about 50° to 100° C, that is to say a temperature from about 100° to 250° C. In this second condensation approximately equimolecular proportions are normally used as well.

Suitable inert organic solvents, as referred to above, are especially those which boil above about 160° C, for example higher benzene-hydrocarbons or halogenated benzenes such as dichlorobenzenes or trichlorobenzenes.

Alternatively, the second amide grouping may be introduced by semi-hydrolysis of the amide-ester obtained in the first stage to form the amide-acid which is converted into the amide-acid halide, and this is followed by amidation of the acid halide group.

In such primarily obtained oxalic acid diarylamides, which still contain free hydroxyl groups, these groups may or must be etherified or esterified in known manner to satisfy the above general formulae.

According to a preferred process for the manufacture of asymmetrical oxalic acid diarylamides of the formula (1) the carboxyl groups or carboxylate groups of the oxalic acid or of its semi-esters or diesters are reacted with primary aromatic amines in the presence of anhydrous boric acid (in the melt or in the presence of an inert solvent) in an amount of 0.1 to 5% of the weight of the oxalic acid or of its ester.

Thus, in the case of compounds of the formula (1), the second stage consists in the condensation of an oxalic acid derivative of the formula

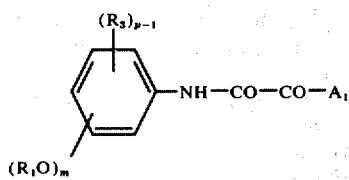

with an amine of the formula

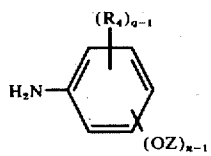

where $R_1$, $R_3$, $R_4$, $m$, $n$, $p$ and $q$ have the above meanings; $A_1$ is a hydroxyl group, a halogen atom or an alkoxy group with 1 to 12 carbon atoms, or a group -O-benzyl or -O-phenyl, and Z stands for a hydrogen atom or equals $R_2$ as defined above - at a temperature from 50° to 250° C, and then free hydroxyl groups are blocked by subsequent etherification or acylation.

Thus, taking into consideration the above statements, the preferred variant of the process for the manufacture of compounds of the general formula (1) consists in condensing an oxalic acid derivative of the formula

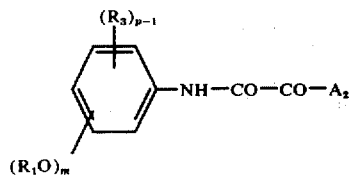

with an amine of the formula

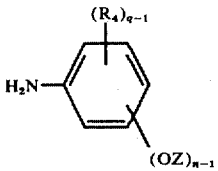

(where $R_1$, $R_3$, $R_4$, Z, $m$, $n$, $p$ and $q$ have the above meanings and $A_2$ represents an alkoxy group with 1 to 12 carbon atoms) in the melt or in a solvent that is inert towards the reactants, in the presence of anhydrous boric acid, at a temperature from 100° to 250° C, whereupon free hydroxyl groups are blocked by etherification or acylation.

In this condensation it is advantageous to use 0.1 to 5% of anhydrous boric acid referred to the weight of oxalic acid derivative, and to use a reaction temperature from 150° to 200° C.

Within the scope of the requirements of formula (1) there may be used in the present process, for example, the following amines to form in each case one of the two amide groupings:

Aniline, 2-, 3- and 4-chloraniline,
2,4- and 3,4-dichloraniline,
2,4,6-trichloraniline and the corresponding bromanilines,
2-, 3- and 4-fluoraniline,
2- and 4-iodaniline,
3,5-diiodaniline,
2-, 3- and 4-methylaniline,
2,4- and 2,5-dimethylaniline,
2,6-diethylaniline,
2-methyl-5-isopropylaniline,
2-, 3- and 4-methoxyaniline,
2,4- and 2,5-dimethoxyaniline,
2,5-diethoxyaniline,
4-butoxyaniline,
3-trifluoromethylaniline,
3,5-bis-trifluoromethylaniline,
2-, 3- and 4-nitraniline,
3- and 4-hydroxyaniline,
2-aminodiphenyl,
meta- and para-aminoacetanilide,
3- and 4-aminobenzoic acids and their amides,
anthranilic acid and its methyl and ethyl esters,
para-amino-N,N-dimethylaniline,
4-amino-methylbenzoate and -ethylbenzoate,
metanilic acid, sulphanilic acid, metanilamide, sulphanilamide,
4-hydroxy-3,5-di-tertiary butylaniline,
4-hydroxy-3,5-dichloraniline,
4,5-dichlorosulphanilic acid,
2-methoxy-5-methylaniline,
4-methyl-3-chloraniline,
2-chloro-4-trifluoromethylaniline,
2,4-dimethoxy-5-chloraniline and
2,4-dimethyl-6-nitraniline.

From among suitable naphthylamines there may be mentioned: α- and β-naphthylamine,
sulphonic acids of the naphthylamines such as
1-naphthylamine-4-, -5- and -8-sulphonic acid,
2-naphthylamine-1- and -5-sulphonic acid,
2-naphthylamine-4,8- and -6,8-disulphonic acid,
8-hydroxy-1-naphthylamine-4-sulphonic acid,
8-hydroxy-2-naphthylamine-6-sulphonic acid,
8-hydroxy-1-naphthylamine-4,6- and -3,6-disulphonic acid and
8-hydroxy-2-naphthylamine-3,6-disulphonic acid.

Hydroxyamines in which a hydroxyl group in ortho-position to the amide nitrogen atom must subsequently be etherified:
2-hydroxyaniline,
2-hydroxy-4- and -5-phenylamine,
2-hydroxy-5-methylaniline,
2-hydroxy-5-chloraniline,
2-hydroxy-5-isooctylaniline,
2-hydroxy-5-dodecylaniline,
2-hydroxy-4-methoxyaniline,
2,4-dihydroxyaniline,
1-hydroxy-2-naphthylamine and
2-hydroxy-1-naphthylamine.

Protection by stabilization can be given with the aid of the oxalic acid diamides described above, in principle, to all those organic materials that are in any form damaged or destroyed by the action of ultraviolet rays. Such damages by the action of the same agency, namely ultraviolet rays, may have very different effects, for example colour shifts, changes in mechanical properties (brittleness, fissuring, tear strength, flexural strength, abrasion resistance, elasticity, ageing), triggering off of undesired chemical reactions (decomposition of delicate chemical substances, for example medicaments), photochemically induced rearrangements, oxidation and the like (for example of oils containing unsaturated fatty acids), causing of burns and irritations (for example on human skin) and the like. Of special importance is the use of the asymmetrical oxalic acid diarylamides defined above for protecting polycondensates and polyadducts from the action of ultraviolet rays.

The organic materials to be protected may be in widely differing processing stages and physical states, their common characteristic being their sensitivity towards ultraviolet rays.

As high-molecular and low-molecular substances that can be protected or stabilized by the present process there may be mentioned, for example, without any limitation thereto: Organic natural substances such as are used for pharmaceutical purposes (medicaments), dyestuffs sensitive to ultraviolet rays compounds which as victuals or in victuals are decomposed by the action of light (unsaturated fatty acids in oils) and the like.

As examples of high-molecular organic substances there may be mentioned:

I. Synthetic organic materials of high or higher molecular weight such as:
  a. Polymerization products based on organic compounds containing at least one polymerizable carbon-to-carbon double bond, that is to say their homopolymers or copolymers as well as their after-treating products, for example crosslinking, grafting or decomposition products; diluted polymers; modification products obtained by modifying reactive groupings in the polymer molecule and the like, for example polymers based on $\alpha,\beta$-unsaturated carboxylic acids (for example acrylates, acrylamides, acrylonitrile) of olefinic hydrocarbons, for example $\alpha$-olefines, ethylene, propylene or dienes, that is to say also rubber and rubber-like polymers (also so-called ABS polymers), polymers based on vinyl and vinylidene compounds (for example styrene, vinyl esters, vinylchloride, vinyl alcohol), of halogenated hydrocarbons, of unsaturated aldehydes and ketones, allyl compounds and the like;
  b. other polymerization products obtainable, for example, by ring opening, for instance polyamides of the polycaprolactam type, also formaldehyde polymers, or polymers accessible by polyaddition or polycondensation, such as polyethers, polythioethers, polyacetals, thioplasts;
  c. polycondensation products or precondensates based on bifunctional or polyfunctional compounds containing condensable groups, their homocondensates and cocondensates as well as their after-treatment products, such, for example, as polyesters, [saturated (e.g. polyethylene terephthalate) or unsaturated (e.g. maleic acid-dialcohol polycondensates and their crosslinked products with copolymerizable vinyl monomers), linear or branched (also those based on polyhydric alcohols, e.g. alkyd resins)], polyamides (e.g. hexamethylenediamine adipate), maleinate resins, melamine resins, phenolic resins (e.g. novolaks), aniline resins, furan resins, carbamide resins and their precondensates and similarly constituted products; polycarbonates, silicone resins and the like;
  d. polyadducts, such as polyurethanes (crosslinked and not crosslinked); epoxy resins.

II. Semisynthetic organic materials, for example, cellulose esters and mixed esters (cellulose acetate or propionate), nitrocellulose, cellulose ethers, regenerated cellulose (viscose rayon, cuprammonium cellulose) or their after-treatment products; casein synthetics.

III. Natural organic materials of animal or vegetable origin, for example those based on cellulose or proteins such as wool, cotton, silk, bast, jute, hemp, pelts and hairs, leathers, finely divided wood pulp, natural resins (such as colophony, especially lacquer resins), gelatin, glues, also rubber, gutta percha, balata and their after-treatment and modification products, degradation products, products accessible by modification of reactive groups.

The organic materials concerned, especially synthetic materials such as polymers of vinylchloride, saturated and unsaturated polyesters, celluloses and polyamides, may be at widely differing stages of their processing (raw materials, semi-finished products or finished products) and physical states. They may be in the form of products shaped in a wide variety of ways, that is to say, for example, as predominantly three-dimensional objects such as sections, vessels or components of a great variety, chips or granules, foamed products; predominantly two-dimensional materials such as films, foils, lacquers, impregnations or coatings, or predominantly unidimensional materials such as filaments, fibres, flocks, bristles or wires. The said materials may also be in unshaped states in a wide variety of homogeneous or inhomogeneous forms of distribution and physical states, for example in the form of powders, solutions, normal and reversed emulsions (creams), dispersions, latices, sols, gels, putties, waxes, adhesives or pore fillers, and the like.

Fibrous materials may be used in a wide variety of processing forms of non-textile materials, for example as threads, yarns, fibre fleeces, padding, felts, flocculated materials or as textile fabrics or textile laminates, knitwear, papers, cardboards and the like.

The new stabilizers may also be used, for example, as follows:
  a. In cosmetics, such as perfumes, dyed or undyed soaps and bath salts, skin and face creams, powders, repellants and especially sunburn oils and creams;
  b. in admixture with dyestuffs or pigments or as additives to dyebaths, printing, discharge or reserve pastes, also for after-treating dyeings, prints or discharge prints;
  c. in admixture with so-called carriers, antioxidants, other light filters, heat stabilizers or chemical bleaches;
  d. in admixture with crosslinking agents or dressing agents such as starch or synthetically produced dressings;
  e. in combination with detergents (the detergents and stabilizers may, if desired, be added separately to the washing liquors);
  f. in gelatin layers used in photography;
  g. in combination with polymeric vehicles (products of polymerization, polycondensation or polyaddition) in which the stabilizers, if desired in addition to other substances, are incorporated in the dissolved or dispersed form, for example in coating, impregnating or binding agents (solutions, dispersions, emulsions) for textiles, fleeces, paper leathers;
  h. as additives to a wide variety of industrial products to reduce the speed of their ageing, for example as additives to glues, adhesives, paints or the like.

If the protective compounds of this invention are to be used for the treatment of textile organic materials of natural or synthetic origin, for example textile fabrics, they may be applied to the substrate to be protected at any desired phase of the final processing of the latter, such as during a dressing or anticrease finishing or dyeing process or during any other finishing operation, by way of a fixing operation similar to a dyeing process.

Furthermore, the new stabilizers to be used according to this invention are preferably added to or incorporated with the materials prior to or during their shaping. Thus, for example, they may be added to the moulding or injection moulding compositions used in the manufacture of films, foils, tapes or mouldings, or they may be dissolved or dispersed or in any other way finely distributed in the spinning mass before it is spun. The protective compounds may also be added to the starting substances, reaction mixtures or intermediates used in the manufacture of fully synthetic or semisynthetic organic materials, that is to say also before or during the chemical reaction, for example in a polycondensation (including precondensates), in a polymerization (including prepolymers) or in a polyaddition.

An important sphere of application of the stabilizers to be used in the invention consists in incorporating these substances in a protective layer used to protect material placed underneath it. This application may take the form of applying the ultraviolet absorber to the surface layer (of a film or of a fibre or of a multidimensional shaped object). This can be done for example similar to a dyeing process, or the active substance may be embedded in a polymer (polycondensate or polyadduct) film by one of the known surface coating methods with polymeric substances, or the active substance may be dissolved in a suitable solvent and caused to diffuse or swell into the surface layer. According to another important variant the ultraviolet absorber is embedded in a self-supporting, substantially two-dimensional carrier material, for example a foil or the wall of a vessel, in order to keep ultraviolet rays away from the substance located behind it (relevant examples: shop windows, films, transparent packages, bottles).

From the foregoing it is self-evident that in addition to the protection of the substrate or carrier material containing the ultraviolet absorber also other substances contained in the substrate are protected, for example dyestuffs, antioxidants, disinfectants, antistatics and other dressing agents, plasticizers and fillers.

Depending on the type of substance to be protected or stabilized, on its sensitivity or on the form in which the protection and stabilization is to be imparted, the requisite amount of stabilizer may vary within wide limits, for example from about 0.01 to 10% by weight, referred to the amount of substrate to be protected. For most practical purposes, however, a quantity from about 0.05 to 2% will suffice.

Accordingly, as results from the foregoing, the process for protecting organic materials from the effects of ultraviolet radiation and heat consists in homogeneously distributing the oxalic acid diamides described in the organic material to be protected, or applying it to the surface of said material or coating the material to be protected with a filter layer containing one of the compounds mentioned.

In particular, this is advantageously done by homogeneously incorporating the oxalic acid diarylamides described in substance or in the dissolved or dispersed form in an amount of 0.1 to 10%, preferably 0.2 to 2.0% by weight (referred to the weight of the material to be protected) in the organic material to be protected before the latter undergoes its final shaping.

If the substance to be used according to this invention is to be applied to the surface of the substrate to be protected, thus for instance a fibrous material (fabric), this is advantageously done by immersing the substrate to be protected in a liquor in which the ultraviolet absorber is dissolved or dispersed. Suitable relevant solvents are, for example, methanol, ethanol, acetone, ethyl acetate, methylethylketone, cyclohexanol and above all water. The substrate to be treated is left in the liquor for some time, similar to the way that dyeing processes are carried out; as a rule, 10 minutes to 24 hours at 10° to 120° C suffice, during which, if desired, the liquor may be agitated. Finally, the material is rinsed, if necessary washed, and dried.

In many cases it is advantageous to use the light filters described above in combination with sterically hindered phenols esters of thiodipropionic acid or organic phosphorus compounds.

Unless otherwise indicated, parts and percentages in the following Manufacturing Instructions and Examples are by weight.

EXAMPLE 1

A mixture of 22.3 parts of the compound of the formula

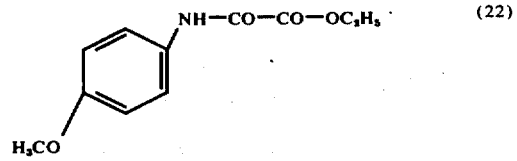

[prepared by condensing the oxalic acid diester $H_5C_2OCO-COOC_2H_5$ with para-anisidine in an anhydrous medium containing a catalytic amount of anhydrous boric acid at a temperature from 110° to 115° C], 10.9 parts of 2-amino-1-phenol and 0.5 part of boric acid is stirred for 2 hours at 175° to 180° C, while continuously distilling off the alcohol formed. The melt is dissolved in dimethylformamide and the solution is mixed with water at 20° C. The product of the formula

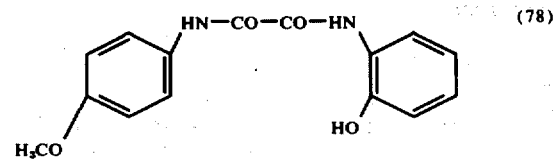

settles out in the form of almost colourless crystals. Yield: about 26 parts. An analytically pure product obtained by three recrystallizations from chlorobenzene melts at 213° –214° C and reveals the following data:

| $C_{15}H_{14}O_4N_2$ | calculated: | C 62.93 | H 4.93 | N 9.79% |
|---|---|---|---|---|
| | found: | 63.09 | 5.04 | 9.86% |

2.9 Parts of the compound of the formula (23) are dissolved in a mixture of 10 parts of acetone and 0.4 part of sodium hydroxide in 10 parts of water. 0.1 Part of sodium carbonate is added and at 20° C within 5 minutes 1.4 parts of dimethylsulphate are dropped in. The batch is stirred for another 4 hours at 45° C, mixed with methanol, cooled to 0° C, and the product of the formula (24)

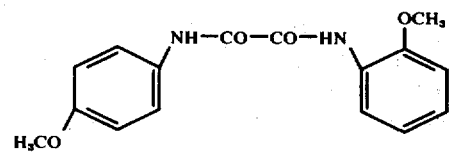

is suctioned off. Yield: about 2.5 parts.

An analytically pure specimen of the product obtained after two crystallizations from benzene melts at 160° –161° C and reveals the following data:

| $C_{16}H_{16}O_4N_2$ | calculated: | C 63.99 | H 5.37 | N 9.33% |
|---|---|---|---|---|
| | found: | 63.98 | 5.43 | 9.31% |

EXAMPLE 2

A solution of 5.8 parts of the compound of the formula (23) in 20 parts of dimethulsulphoxide and 0.8 part of sodium hydroxide is mixed at 20° C with 6.7 parts of n-octadecylbromide, the temperature is raised within 30 minutes to 45° C and the whole is stirred on for 4 hours at the same temperature. The crystalline magma is then mixed with methanol and the product of the formula

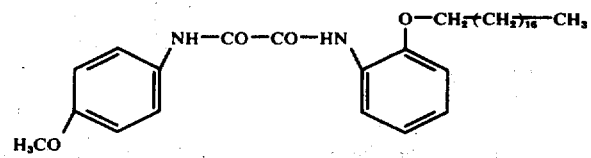

(25)

obtained in the form of colourless crystals is suctioned off. Yield: about 10 parts.

An analytically pure specimen obtained after two crystallizations from hexane melts at 90.5° to 91.5° C and reveals the following data:

| $C_{33}H_{50}O_4N_2$ | calculated: | C 73.56 | H 9.35 | N 5.20% |
|---|---|---|---|---|
| | found: | 73.81 | 9.46 | 5.25% |

EXAMPLE 3

A mixture of 9 parts of the compound of the formula

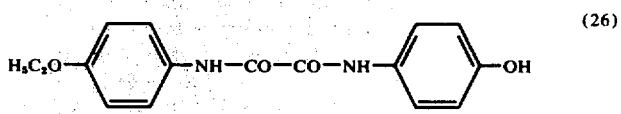

(26)

[prepared as described for compound (23) in Example 1] in 40 parts of dichlorobenzene and 5.4 parts of capryloylchloride is heated for 2 hours at 120° C and then for ½ hour at 140° C, during which the mixture dissolves. It is then cooled at 80° C, 50 parts of hot ethanol are added, the whole is cooled and the precipitate suctioned off. The product (11.5 parts) is washed with alcohol and dried at 60° C in vacuo; it corresponds to the formula

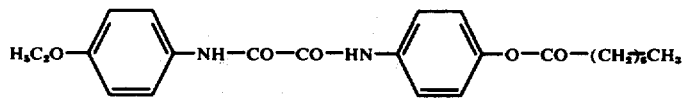

(27)

and melts at 219 to 221° C after recrystallization from chlorobenzene+alcohol. Analytical data:

| $C_{24}H_{30}O_5N_2$ | calculated: | C 67.58 | H 7.09 | N 6.57% |
|---|---|---|---|---|
| | found: | 67.65 | 6.98 | 6.64% |

The compounds listed in the following Tables were obtained in an identical or a similar manner. In these

Tables

| Column I | = formula N° |
|---|---|
| column II | = definition of the compound |
| column III | = melting point in ° C (uncorrected) |
| column IV | = analytical data C H N |
| | (1st line: calculated, 2nd line: found) |

Concerning compound N° 104 in Table $X_3$ it should be mentioned that the $C_{12}H_{25}$-residue is a mixture of differently branched isomers (from tetramerization of 4 propylene molecules) Remark: in Tables $X_5$ to $X_{18}$, $X_{21}$, $X_{23}$ to $X_{25}$ there are shown on the right of the general basic formula the melting point and the analytical data of the starting compound (X = H) used as intermediate.

$X_1$

-continued
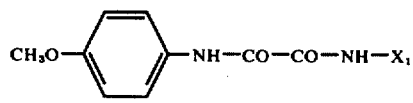
(28)
| I | II ($X_1$=) | III | IV |
|---|---|---|---|
| 29. | 2,4-(CH₃)₂-phenyl | 196–197 | 68.44 6.08 9.39 / 68.31 6.06 9.53 |
| 30. | 3,5-(CH₃)₂-phenyl | 191–192 | 68.44 6.08 9.39 / 68.56 5.94 9.43 |
| 31. | 3,5-Cl₂-phenyl | 233–234 | 53.12 3.57 8.26 / 53.09 3.47 8.26 |
| 32. | 3-CF₃-5-Cl-phenyl | 198–199 | 51.90 3.48 7.50 / 51.91 3.26 7.39 |
| 33. | 3,5-(CF₃)₂-phenyl | 182–183 | 50.26 2.98 6.90 / 50.82 2.79 7.04 |
| 34. | 1-naphthyl | 198–199 | 71.24 5.03 8.75 / 71.32 4.92 8.67 |
| 35. | 2-CH₃-4-Cl-phenyl | 166–167 | 60.29 4.74 8.79 / 60.14 4.48 8.88 |
| 36. | 3-CH₃-phenyl | 194–195 | 67.59 5.67 9.85 / 67.56 5.70 9.84 |
$X_2$ -continued
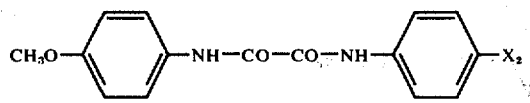
(37)
| I | II ($X_2=$) | III | | |
|---|---|---|---|---|
| 38. | —$CH_3$ | 230– | 67.59 | 5.67 9.85 |
| | | 231 | 67.40 | 5.42 9.83 |
| 39. | —Br | 280– | 51.60 | 3.75 8.02 |
| | | 281 | 51.69 | 3.86 7.98 |
| 40. | —Cl | 267– | 59.12 | 4.30 9.19 |
| | | 268 | 59.28 | 4.28 9.11 |
| 41. | —$N(CH_3)_2$ | 243– | 65.16 | 6.11 13.41 |
| | | 244 | 64.90 | 6.03 12.82 |
$X_3$
| I | II | III | IV |
|---|---|---|---|
| 42. | 2-$OC_2H_5$, 2'-$OC_2H_5$, 5'-$OC_2H_5$ diphenyl oxamide | 122–<br>123 | 64.50 6.50 7.52<br>64.50 6.37 7.72 |
| 43. | 4-$OC_2H_5$-phenyl / 2,4,6-tri$CH_3$-phenyl oxamide | 237–<br>239 | 69.92 6.79 8.58<br>69.65 6.74 8.46 |
| 44. | 2-$OCH_3$,4-$OCH_3$-phenyl / 3,5-di$CH_3$-phenyl oxamide | 157–<br>158 | 65.84 6.14 8.53<br>66.09 6.24 8.72 |
| 45. | 2-$OCH_3$,4-$OCH_3$-phenyl / 3-$C(CH_3)_3$,4-$OC_8H_{17}$-phenyl oxamide | 110–<br>111 | 69.39 8.32 5.78<br>69.49 8.20 5.87 |
| 46. | 2-$OCH_3$,4-$OCH_3$-phenyl / 3-$C(CH_3)_3$,4-$OCH_3$-phenyl oxamide | 184–<br>185 | 65.27 6.78 7.25<br>65.16 6.88 7.33 |
| 47. | 4-$OC_2H_5$-phenyl / 2-biphenyl oxamide | 147–<br>148 | 73.31 5.59 7.77<br>73.16 5.51 7.94 |

| | | | |
|---|---|---|---|
| 48. | 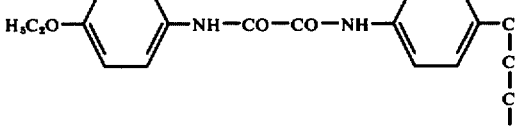 H₃C₂O—⌬—NH—CO—CO—NH—⌬—CH₂CH₂CH₂CH₃ (isobutyl chain shown) | 222–<br>223 | 69.92 7.09 8.14<br>70.12 7.12 8.33 |
| 49. |  H₃C₂O—⌬—NH—CO—CO—NH—⌬—CH₂COOH | 267–<br>268 | 63.15 5.30 8.18<br>62.90 5.33 8.27 |
| 50. | 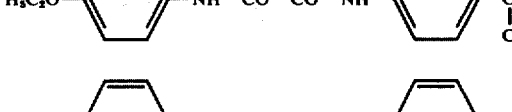 H₃C₂O—⌬—NH—CO—CO—NH—⌬—C₁₂H₂₅ | 129–<br>138 | 74.30 8.91 6.19<br>74.36 8.69 6.25 |
X₄
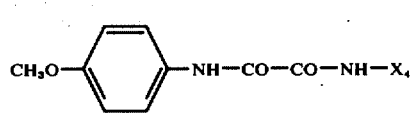
CH₃O—⌬—NH—CO—CO—NH—X₄  (51)
| I | II | III |
|---|---|---|
| 52. | 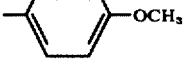 2,5-dimethoxyphenyl (OCH₃, OCH₃) | 174–  61.81 5.49 8.48<br>175    62.09 5.34 8.48 |
| 53. | 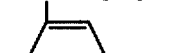 O—CH₂CH₂Cl phenyl | 190–  59.59 5.28 7.72<br>191    59.28 5.01 7.71 |
| 12. | 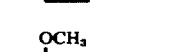 OCH₃, C(CH₃)₃ phenyl | 173–  67.39 6.79 7.86<br>174    67.17 6.90 7.94 |
| 54. |  OC₈H₁₇, C(CH₃)₃ phenyl | 93–   71.33 8.43 6.16<br>94     71.59 8.44 6.25 |
| 55. | 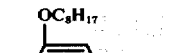 OC₈H₁₇ phenyl | 92–   69.32 7.59 7.03<br>93     69.43 7.72 7.13 |
| 56. | 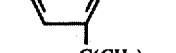 OCH₃, OCH₃, Cl phenyl | 189–  55.98 4.70 7.68<br>190    56.03 4.77 7.73 |
| I | II | III | IV |
|---|---|---|---|

-continued
| | | | | | |
|---|---|---|---|---|---|
| 57. | 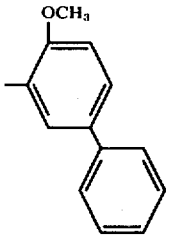 OCH₃ | | 187–<br>188 | 70.20 5.36 7.44<br>70.43 5.49 7.44 | |
| 16. | 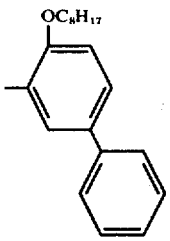 OC₈H₁₇ | | 144–<br>146 | 73.39 7.22 5.90<br>73.79 7.25 5.90 | |
| 58. | 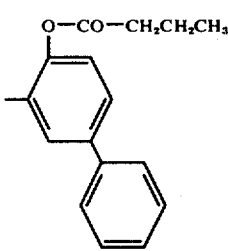 O—CO—CH₂CH₂CH₃ | | 135–<br>137 | 69.43 5.59 6.48<br>69.49 5.58 6.55 | |
$X_5$
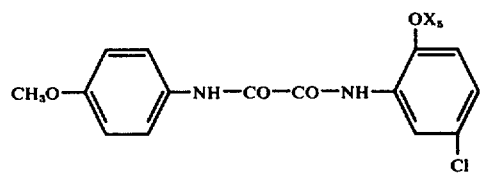
(59)
$X_5 =$ H : 236– 56.17 4.09 8.73
237   56.17 4.02 8.67
| I | II | III | IV |
|---|---|---|---|
| 60. | —CH₃ | 169–<br>170 | 57.41 4.52 8.37<br>57.34 4.38 8.43 |
| 61. | —CH₂CH₂CH₂Cl | 130–<br>131 | 54.42 4.57 7.05<br>54.52 4.48 7.04 |
| 62. | —(CH₂)₁₉—CH₃ | 92–<br>93 | 69.15 8.62 4.89<br>69.20 8.67 5.01 |
$X_6$
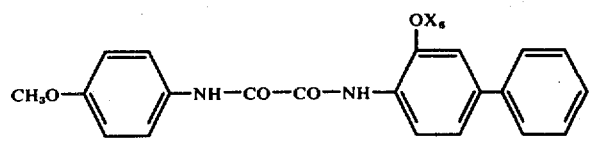
(63)
| I | II ($X_6 =$) | III | IV |
|---|---|---|---|
| 64. | —CH₃ | 188–<br>189 | 70.20 5.36 7.44<br>70.04 5.11 7.63 |
| 65. | —C₈H₁₇ | 145–<br>146 | 73.39 7.22 5.90<br>73.45 7.29 5.81 |
| 66. | —CH₂—COOC₂H₅ | 193–<br>194 | 66.90 5.39 6.24<br>66.91 5.35 6.23 |
| 67. | —CH₂CH₂CH₂—Cl | 160–<br>161 | 65.68 5.28 6.38<br>65.26 5.42 6.47 |
$X_7$ -continued
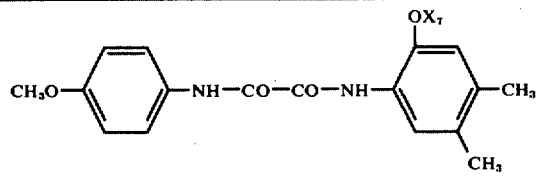
(68)
X₇ = H : 226— 64.95 5.77 8.91
227 65.07 5.80 8.82
| I | II (X₇=) | III | IV |
|---|---|---|---|
| 69 | —CH₃ | 163— | 65.84 6.14 8.53 |
| | | 164 | 65.79 6.24 8.61 |
| 70 | —C₈H₁₇ | 116— | 70.39 8.03 6.57 |
| | | 117 | 70.69 7.97 6.69 |
| 71 | —CH₂CH₂CH₂Cl | 131— | 61.46 5.93 7.17 |
| | | 132 | 61.20 5.97 7.13 |
X₈
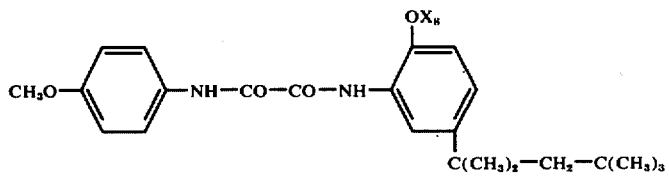
(72)
X₈ = H : 226— 69.32 7.59 7.03
228 69.15 7.36 7.16
| I | II (X₈ =) | III | IV |
|---|---|---|---|
| 14. | —CO—CH₃ | 154— | 68.16 7.32 6.36 |
| | | 155 | 68.23 7.20 6.43 |
| 73. | —CO—(CH₂)₁₀—CH₃ | 56— | 72.13 9.34 4.81 |
| | | 57 | 72.55 9.05 4.92 |
| 74. | —CH₃ | 152— | 69.88 7.82 6.79 |
| | | 154 | 70.02 7.76 6.74 |
| 75. | —(CH₂)₇—CH₃ | 86— | 72.90 9.08 5.49 |
| | | 88 | 72.54 8.86 5.70 |
| 76. | —CH₂—CH=CH₂ | 116— | 71.20 7.82 6.39 |
| | | 118 | 71.44 7.80 6.46 |
| 77. | —CH₂—C₆H₅ | 104— | 73.69 7.43 5.73 |
| | | 106 | 73.48 7.55 5.70 |
X₉
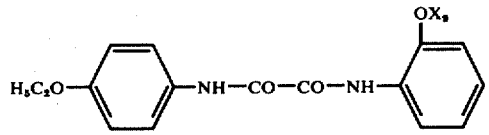
(78)
X₉=H : 229— 63.99 5.37 9.30
230 64.05 5.51 9.19
| I | II (X₉=) | III | IV |
|---|---|---|---|
| 79. | —CH₃ | 155— | 64.95 5.77 8.91 |
| | | 156 | 64.97 5.82 9.01 |
| 80. | —CO—CH=CH₂ | 150— | 64.40 5.10 7.90 |
| | | 151 | 64.06 5.12 7.87 |
| 81. | —C₈H₁₇ | 94— | 69.88 7.82 6.79 |
| | | 95 | 69.83 7.55 6.76 |
| 82. | —CH₂CH₂CH₂Cl | 139— | 60.56 5.62 7.43 |
| | | 140 | 60.70 5.56 7.61 |
| 83. | —CH₂—C₆H₅ | 166— | 70.75 5.68 7.18 |
| | | 167 | 70.81 5.71 7.39 |
| 84. | —CH₂—COOC₂H₅ | 152— | 62.16 5.74 7.25 |
| | | 153 | 62.28 5.72 7.51 |
| 85. | —CO—CH₃ | 147— | 63.15 5.30 8.18 |
| | | 148 | 63.89 5.84 8.10 |

-continued
| | | | |
|---|---|---|---|
| 86. | —CH₂CH₂—O—CH₂CH₂—CN | 131– | 63.46 5.83 10.58 |
| | | 132 | 63.89 5.84 10.13 |
| 87. | —CH₂—COOH | 193– | 60.33 5.06 7.82 |
| | | 194 | 60.37 5.11 7.77 |
| 88. | —CH₂—CONH—C₆H₅ | 252– | 65.54 5.50 9.97 |
| | | 253 | 65.62 5.31 9.66 |
| 89. | —CH₂—COOC₁₂H₂₅ | 115– | 68.41 8.04 5.32 |
| | | 116 | 68.19 7.79 5.33 |
| 90. | —CO—C₆H₅ | 167– | 68.30 4.99 6.93 |
| | | 168 | 68.21 5.13 6.96 |
| 91. | —CO—C₆H₄—Cl | 205– | 62.95 4.36 6.38 |
| | | 206 | 62.92 4.41 6.53 |
| 92. | —CO—C₆H₄—C(CH₃)₃ | 182– | 70.42 6.13 6.08 |
| | | 183 | 70.06 6.45 6.36 |
| 93. | —CO—NH—C₄H₉ | 161– | 63.14 6.31 10.52 |
| | | 162 | 63.19 6.21 10.36 |
$X_{10}$
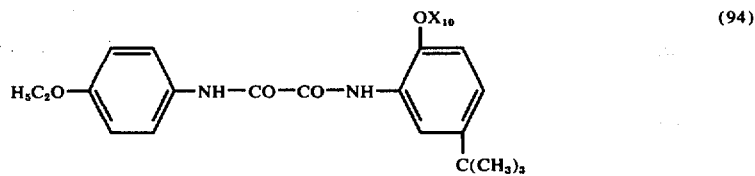
(94)
X₁₀ = H : 226– 67.39 6.79 7.86
227 67.19 6.74 7.91
| I | II (X₁₀=) | III | IV |
|---|---|---|---|
| 95. | —CH₃ | 161– | 68.09 7.07 7.56 |
| | | 162 | 68.03 6.94 7.82 |
| 96. | —C₄H₉ | 124– | 69.88 7.82 6.79 |
| | | 125 | 70.05 7.93 6.62 |
| 97. | —C₈H₁₇ | 90– | 71.76 8.60 5.98 |
| | | 91 | 71.71 8.71 6.05 |
| 98. | —C₁₂H₂₅ | 94– | 73.24 9.22 5.34 |
| | | 95 | 73.29 9.18 5.54 |
| 99. | —C₁₈H₃₇ | 98– | 74.95 9.93 4.60 |
| | | 99 | 75.25 10.10 4.87 |
| 100. | —CO—CH=CH₂ | 151– | 67.30 6.39 6.83 |
| | | 152 | 67.47 6.43 6.97 |
$X_{11}$
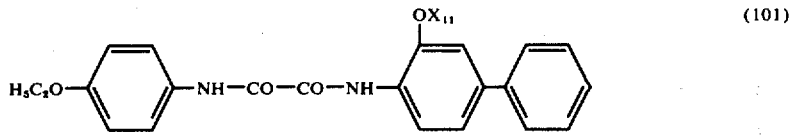
(101)
X₁₁=H : 267– 70.20 5.36 7.44
268 70.12 5.47 7.32
| I | II (X₁₁=) | III | IV |
|---|---|---|---|
| 102. | —CH₃ | 186– | 70.75 5.68 7.18 |
| | | 187 | 71.00 5.82 7.11 |
| 103. | —C₄H₉ | 181– | 72.20 6.53 6.48 |
| | | 182 | 72.23 6.70 6.66 |
| 104. | —C₈H₁₇ | 158– | 73.74 7.43 5.73 |
| | | 159 | 73.96 7.44 5.77 |
| 105. | —C₁₂H₂₅ | 150– | 74.96 8.14 5.14 |
| | | 151 | 75.33 8.21 5.02 |

-continued
| | | III | IV |
|---|---|---|---|
| 106. | —C₁₈H₃₇ | 135– | 76.39 8.98 4.46 |
| | | 136 | 76.55 9.02 4.46 |
| 107. | —CH₂—(phenyl) | 185– | 74.66 5.62 6.01 |
| | | 186 | 74.46 5.59 6.05 |
| 108. | —CH₂—COOC₂H₅ | 198– | 67.52 5.67 6.06 |
| | | 199 | 67.43 5.61 6.13 |
| 109. | —CO—CH₃ | 201– | 68.89 5.30 6.70 |
| | | 202 | 68.86 5.53 6.96 |
$X_{12}$
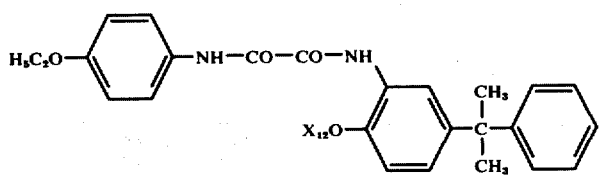
(110)
$X_{12}$=H : 211– 71.75 6.26 6.69
213  71.54 6.09 6.89
| I | II ($X_{12}$=) | III | IV |
|---|---|---|---|
| 111. | —C₂H₅ | 155– | 72.62 6.77 6.27 |
| | | 156 | 72.53 6.65 6.35 |
| 112. | —C₈H₁₇ | 88– | 74.68 7.98 5.28 |
| | | 89 | 74.49 7.94 5.40 |
$X_{13}$
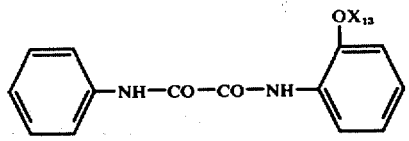
(113)
$X_{13}$=H : 261– 65.62 4.72 10.93
262  65.64 4.82 11.13
| I | II ($X_{13}$=) | III | IV |
|---|---|---|---|
| 114. | —CH₃ | 170– | 66.65 5.22 10.37 |
| | | 171 | 66.69 5.33 10.16 |
| 115. | —CH₂CH₂CH₂Cl | 91– | 61.36 5.15 8.42 |
| | | 92 | 61.30 5.24 8.64 |
| 116. | —C₈H₁₇ | 86– | 71.71 7.66 7.60 |
| | | 87 | 71.95 7.64 7.58 |
| 117. | —CH₂—(phenyl) | 167– | 72.82 5.24 8.09 |
| | | 168 | 73.15 5.25 7.91 |
$X_{14}$
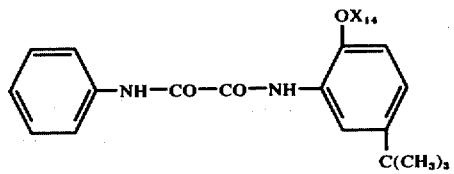
(118)
$X_{14}$=H : 201– 69.21 6.45 8.97
202  68.99 6.36 9.00
| I | II ($X_{14}$=) | III | IV |
|---|---|---|---|
| 119 | —CH₃ | 132– | 69.92 6.79 8.58 |
| | | 133 | 69.94 6.86 8.85 |
| 120 | —CH₂CH₂CH₂Cl | 96– | 64.86 6.48 7.20 |
| | | 97 | 64.98 6.24 7.21 |
| 121 | —C₈H₁₇ | 99– | 73.55 8.55 6.60 |
| | | 100 | 73.79 8.69 6.36 |

-continued
| 122 | 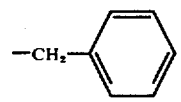 | 182– | 74.60 | 6.51 | 6.96 |
|---|---|---|---|---|---|
|  |  | 183 | 74.75 | 6.58 | 7.03 |
| 123 | —C₁₂H₂₅ | 76– | 74.96 | 9.23 | 5.83 |
|  |  | 77 | 75.15 | 9.40 | 5.92 |
| 124 | —CO—CH₃ | 181– | 67.78 | 6.26 | 7.91 |
|  |  | 182 | 67.98 | 6.25 | 7.95 |
X₁₅
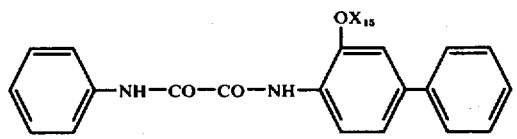
(125)
| I | II (X₁₅=) | III | IV |
|---|---|---|---|
| 126. | —CH₃ | 189– | 72.82 5.24 8.09 |
|  |  | 190 | 72.55 5.26 8.02 |
| 127. | —CH₂—COOC₂H₅ | 182– | 68.89 5.30 6.70 |
|  |  | 183 | 68.93 5.34 6.76 |
| 128. | —C₁₈H₃₇ | 114– | 78.04 8.96 4.79 |
|  |  | 115 | 78.29 8.93 4.74 |
X₁₆
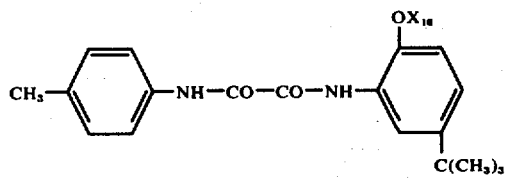
(129)
X₁₆=H : 228– 69.92 6.79 8.58
229 69.71 6.49 8.58
| I | II (X₁₆=) | III | IV |
|---|---|---|---|
| 130 | —CH₃ | 169– | 70.56 7.11 8.23 |
|  |  | 170 | 70.81 7.32 8.12 |
| 131 | —CH₂CH₂CH₂—Cl | 114– | 65.58 6.75 6.95 |
|  |  | 115 | 65.69 6.73 7.23 |
| 132 | —C₈H₁₇ | 92– | 73.94 8.73 6.35 |
|  |  | 93 | 73.98 8.96 6.38 |
| 133 | 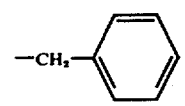 | 171– | 74.97 6.78 6.73 |
|  |  | 172 | 75.04 7.00 6.50 |
X₁₇
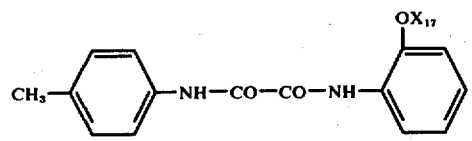
(134)
X₁₇=H : 221– 66.65 5.22 10.37
222 66.70 5.27 10.26
| I | II (X₁₇=) | III | IV |
|---|---|---|---|
| 135. | —CH₃ | 165– | 67.59 5.67 9.85 |
|  |  | 166 | 67.89 5.87 9.81 |
| 136. | —C₄H₉ | 103– | 69.92 6.79 8.57 |
|  |  | 104 | 69.78 6.79 8.32 |
| 137. | —C₈H₁₇ | 95– | 72.22 7.91 7.32 |
|  |  | 96 | 72.52 7.89 7.55 |
X₁₈

-continued
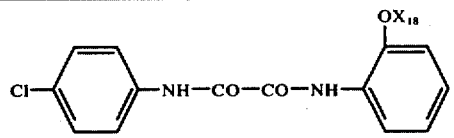
(138)
X₁₈=H : 246– 57.84 3.81 9.64
247 58.00 3.84 9.67
| I | II(X₁₈=) | III | IV | | |
|---|---|---|---|---|---|
| 139. | —CH₃ | 212– | 59.12 | 4.30 | 9.19 |
|  |  | 213 | 59.31 | 4.33 | 9.22 |
| 140. | —C₂H₅ | 187– | 60.29 | 4.74 | 8.79 |
|  |  | 189 | 60.04 | 4.97 | 8.99 |
| 141. | —C₄H₉ | 116– | 62.34 | 5.52 | 8.08 |
|  |  | 117 | 62.42 | 5.51 | 8.02 |
| 142. | —C₈H₁₇ | 94– | 65.58 | 6.75 | 6.95 |
|  |  | 95 | 65.61 | 6.63 | 7.09 |
X₁₉
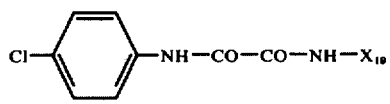
(143)
| I | II (X₁₉=) | III | IV | | |
|---|---|---|---|---|---|
| 144. | (2,4-dimethoxyphenyl) OCH₃ / OCH₃ | 189– | | 4.52 | 8.37 |
|  |  | 190 | 57.42 | 4.29 | 8.33 |
| 145. | (3-octyloxy-biphenyl) OC₈H₁₇ | 147– | 70.21 | 6.52 | 5.85 |
|  |  | 148 | 69.90 | 6.48 | 5.98 |
| 146. | (3-methoxy-4-tert-butylphenyl) OCH₃ / C(CH₃)₃ | 172– | 63.24 | 5.87 | 7.76 |
|  |  | 173 | 62.69 | 5.80 | 7.71 |
| 147. | (2-octyloxy-4-tert-butylphenyl) OC₈H₁₇ / C(CH₃)₃ | 116– | 68.03 | 7.69 | 6.10 |
|  |  | 117 | 68.17 | 7.70 | 5.89 |
X₂₀
| I | II | III | | | |
|---|---|---|---|---|---|
| 148. | NC—C₆H₄—NH—CO—CO—NH—C₆H₄—OC₂H₅ | 217– | 66.01 | 4.89 | 13.59 |
|  |  | 218 | 65.98 | 4.91 | 13.65 |
| 149. | biphenyl-NH—CO—CO—NH—(2-OCH₃-5-C(CH₃)₃-phenyl) | 188– | 74.60 | 6.51 | 6.96 |
|  |  | 189 | 74.55 | 6.65 | 6.97 |

-continued
$X_{21}$
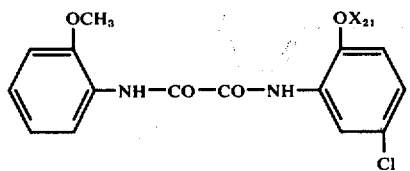
(150)
| I | II ($X_{21}=$) | III | IV |
|---|---|---|---|
| 151. | —CH₃ | 209–210 | 57.41 4.52 8.37 / 57.39 4.49 8.44 |
| 152. | —C₈H₁₇ | 91–92 | 63.81 6.75 6.47 / 64.10 6.76 6.49 |
| 153. | —CH₂CH₂CH₂—Cl | 146–147 | 54.42 4.57 7.05 / 54.32 4.76 7.00 |
| 154. | —CH₂—C₆H₅ | 176–177 | 64.31 4.66 6.82 / 64.68 4.51 6.79 |
| 155. | —CH₂—COOC₂H₅ | 161–162 | 56.10 4.71 6.89 / 56.28 4.65 6.87 |
| 156. | —CO—CH₃ | 167–168 | 56.29 4.17 7.72 / 56.33 4.13 7.81 |
$X_{22}$
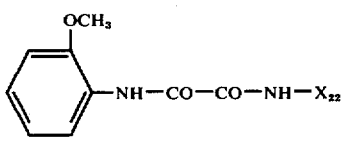
(157)
| I | II ($X_{22}=$) | III | IV |
|---|---|---|---|
| 158. | 2,6-dimethyl-4-tert-butyl-3-(OC₈H₁₇)phenyl | 119–120 | 71.33 8.43 6.16 / 71.21 8.39 6.42 |
| 159. | 2-methyl-(OC₈H₁₇)phenyl | 117–118 | 69.32 7.59 7.03 / 69.59 7.31 7.18 |
| 160. | 2-methyl-(OCH₂CH₂CH₂—Cl)phenyl | 146–147 | 59.59 5.28 7.72 / 59.94 5.17 7.81 |
| 161. | 2-methyl-(O—CH₂—C₆H₅)phenyl | 189–190 | 70.20 5.36 7.44 / 70.25 5.46 7.37 |
| 162. | 2-methyl-(O—CH₂—COOC₂H₅)phenyl | 155–156 | 61.28 5.41 7.52 / 61.06 5.39 7.66 |

-continued
| 163. | 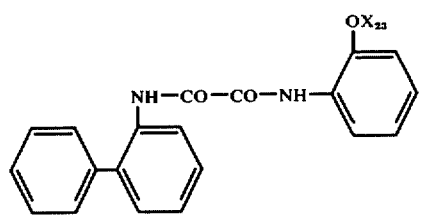 | | 139– | 62.19 | 4.91 | 8.53 |
| --- | --- | --- | --- | --- | --- | --- |
| | | | 140 | 61.93 | 5.01 | 8.76 |
X₂₃
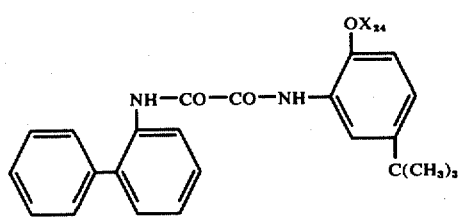 (164)
| | | $X_{23}$ = H : | 203– | 72.28 | 4.85 | 8.43 |
| --- | --- | --- | --- | --- | --- | --- |
| | | | 204 | 72.08 | 4.69 | 8.27 |
| I | II ($X_{23}$=) | | III | IV | | |
| 165. | —CH₃ | | 145– | 72.82 | 5.24 | 8.09 |
| | | | 146 | 72.58 | 5.32 | 8.04 |
| 166. | —C₈H₁₇ | | 105– | 75.65 | 7.26 | 6.30 |
| | | | 106 | 75.58 | 7.40 | 6.41 |
| 167. | —CH₂CH₂CH₂Cl | | 148– | 67.56 | 5.18 | 6.85 |
| | | | 149 | 67.89 | 5.32 | 6.65 |
X₂₄
(168)
| | | $X_{24}$ = H : | 227– | 74.20 | 6.27 | 7.21 |
| --- | --- | --- | --- | --- | --- | --- |
| | | | 228 | 73.63 | 6.34 | 7.24 |
| I | II ($X_{24}$=) | | III | IV | | |
| 169. | —CH₃ | | 190– | 74.60 | 6.51 | 6.96 |
| | | | 191 | 74.70 | 6.56 | 7.16 |
| 170. | —C₈H₁₇ | | 149– | 76.76 | 8.05 | 5.60 |
| | | | 150 | 76.48 | 8.09 | 5.75 |
| 171. | —CH₂—CH₂—CH₂—Cl | | 168– | 69.74 | 6.29 | 6.02 |
| | | | 169 | 69.65 | 6.04 | 6.16 |
| 172. | —CO—CH₃ | | 166– | 72.54 | 6.09 | 6.51 |
| | | | 167 | 72.35 | 6.16 | 6.35 |
| 173. | —CH₂—COOC₂H₅ | | 157– | 70.86 | 6.37 | 5.90 |
| | | | 158 | 70.77 | 6.38 | 6.20 |
X₂₅
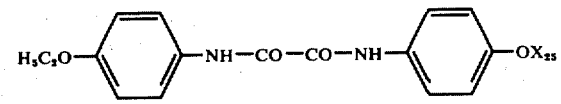 (174)
| | | $X_{25}$=H : | 280– | 63.99 | 5.37 | 9.33 |
| --- | --- | --- | --- | --- | --- | --- |
| | | | 282 | 63.95 | 5.34 | 9.06 |
| I | II ($X_{25}$=) | | III | IV | | |
| 175. | —CO—⌬ (phenyl) | | 270– | 68.30 | 4.99 | 6.93 |
| | | | 272 | 68.21 | 4.88 | 6.94 |

-continued

| | | | |
|---|---|---|---|
| 176. | —CO—⟨benzene⟩—C(CH$_3$)$_3$ | 281–282 | 70.42 6.13 6.08 / 70.60 6.10 6.25 |
| 177. | —CO—NH—CH$_2$CH$_2$CH$_2$CH$_3$ | 272–275 | 63.14 6.31 10.52 / 63.40 6.03 10.31 |
| 178. | —CH$_3$ | 229–230 | 64.95 5.77 8.91 / 64.72 5.54 9.04 |
| 179. | —C$_4$H$_9$ | 228–229 | 67.39 6.79 7.86 / 67.54 6.63 7.94 |
| 180. | —C$_8$H$_{17}$ | 205–206 | 69.88 7.82 6.79 / 69.71 7.52 6.84 |
| 181. | —C$_{12}$H$_{25}$ | 202–203 | 71.76 8.60 5.98 / 71.70 8.50 6.05 |
| 182. | —CH$_2$—⟨benzene⟩ | 245–246 | 70.75 5.68 7.18 / 70.62 5.59 7.26 |
| 183. | —CH$_2$—CH=CH$_2$ | 243–244 | 67.04 5.92 8.23 / 66.91 5.67 8.12 |

EXAMPLES OF USE

EXAMPLE 4

An acetylcellulose film about 50μ thick is produced by pouring out a 10% acetonic solution of acetylcellulose containing 1% [calculated from acetylcellulose] of the compound of the formula (52). The dried film reveals the following light transmission values in percent:

| | Light transmission in percent | |
|---|---|---|
| Wavelength in mμ | unexposed | exposed for 100 hours in a fadeometer |
| 260 to 340 | 0 | 0 |
| 350 | 3 | 3 |
| 360 | 10 | 10 |
| 370 | 30 | 30 |
| 380 | 55 | 55 |

A similar behaviour is observed, for example, with the compound of the formula (39), (79), (92), (114), (144), or (151).

EXAMPLE 5

A paste from 100 parts of polyvinylchloride, 59 parts by volume of dioctylphthalate and 0.2 part of the compound of the formula (24) is rolled to and fro on a calender at 145° to 150° C to form a foil about 0.5mm thick. The polyvinylchloride foil obtained in this manner absorbs ultraviolet light within the region from 280 to 360 mμ.

Instead of the compound of the formula (24) there may be used, for example, the compound of the formula (42), (43), (55), (61), (79), (95), (111), (119), (151), (165) or (176).

EXAMPLE 6

A mixture of 100 parts of polyethylene and 0.2 part of the compound of the formula (53) is rolled to and fro on a calender at 130° to 140° C to form a foil which is then pressed at 150° C.

The polyethylene foil obtained in this manner is substantially impermeable to ultraviolet light within the region from 280 to 350 ,μ.

Instead of the compound of the formula (53) there may be used, for example, the compound of the formula (46), (55), (89), (104), (115), (132), (152) or (166).

EXAMPLE 7

A mixture of 100 parts of polypropylene and 0.2 part of the compound of the formula (12), (65), (81), (111), (123), (132), (142), (152), (153) or (167) is turned on a calender at 170° C into a sheet which is then pressed at 230 to 240° C under a maximum pressure of 40kg/cm$^2$ to form a panel 1 mm thick.

The panels obtained in this manner are substantially impermeable to ultraviolet light within the region from 280 to 360 mμ. Other compounds listed in the Table reveal a similar behavior.

EXAMPLE 8

A solution of 0.2 part of the compound of the formula (24) in 1.8 parts of monostyrene is mixed with 0.5 part of a solution of cobalt naphthenate in monostyrene (containing 1% of cobalt). Then 40 parts of an unsaturated polyester resin based on phthalic acid/maleic acid/ethyleneglycol in monostyrene are added and the whole is stirred for 10 minutes. 1.7 Parts of a catalyst solution (methylethyl ketone peroxide in dimethylphthalate) are dropped in and the well-stirred, air-free mass is poured in between two panes of glass. After about 20 minutes the polyester panel of about 1 mm thickness has sufficiently solidified to be taken out of the mould; it is impermeable to ultraviolet light within the region from 280 to 350 mμ and reveals no sign of yellowing after 1000 hours' exposure in the xeno test.

Instead of the compound of the formula (24) there may be used, for example, the compound of the formula (14), (66), (84), (102), (108), (119), (130), (154) or (169).

EXAMPLE 9

25 Grams of distilled monostyrene are prepolymerized in a stoppered flask in a heating cabinet for 2 days at 90° C. Then 0.25 g of the compound of the formula (50), (58), (61), (70), (100), (121), (163) or (170) and 0.025 g of benzoyl peroxide are slowly stirred into the viscous mass. The mixture is poured into a cubic mould made from aluminium foil and heated for 1 day at 70° C. After the mass has completely cooled and solidified, the mould is broken apart. The resulting block is then pressed in a hydraulic press at 138° C under a pressure of 150 kg/cm² to form a panel 1 mm thick.

The polystyrene panels manufactured in this manner are impermeable to ultraviolet light within the region from 280 to 350 mµ; they are completely colourless. On exposure in a fadeometer a distinct improvement in the stability towards light is observed since polystyrene panels containing a compound of the above formulae display no sign of yellowing after 200 hours' exposure, while panels that do not contain such an absorber have already become yellow. Similar results are obtained with other compounds listed in the Table.

EXAMPLE 10

0.1 Gram of the compound of the formula (67), (73), (84), (99), (124), (135), (152), (167) or (176) is dissolved in 40 g of clear nitrocellulose lacquer of 25% strength. The lacquer is then evenly spread over maple boards with a coating doctor and is completely dry after a short time. The addition of the above-mentioned ultraviolet absorbers does not change the shade of the wood. The light colour of the lacquered wood is not changed either after several days' exposure to the light of an ultraviolet lamp, provided the lacquer contains one of the above-mentioned compounds in a concentration of about 1%. Untreated wood darkens after only a few days' exposure as described.

Similar results are obtained by using acrylic resin lacquers of alkyd-melamine resin lacquers and other compounds listed in the Table.

EXAMPLE 11

8 Grams of a mixture of toluylene-2,4-diisocyanate and toluylene-2,6-diisocyanate (65 : 35) and 20 g of a slightly branched polyester from adipic acid, diethyleneglycol and triol (hydroxyl number: 60) are stirred together for about 15 seconds. The 2 ml of a catalyst mixture (consisting of 6 ml of a tertiary amine, 3 ml of a dispersant, 3 ml of a stabilizer and 2 ml of water) and 0.28 g of the compound (46), (53), (75), (85), (93), (97), (130), (151) or (166) are added and the whole is stirred for a short time. A foam fleece forms which is immersed in water after 30 minutes. After another 30 minutes it is thoroughly washed with water and dried at room temperature.

The addition of one of the aforementioned ultraviolet absorbers improves the stability during the exposure in the xeno test apparatus. The above absorbers also lend themselves well to incorporation with numerous other polyurethanes obtained by the isocyanate polyaddition process.

A similar behaviour is observed also with other compounds listed in the Table.

EXAMPLE 12

10,000 Parts of a polyamide in chip form, prepared in known manner from caprolactam, are mixed for 12 hours with 30 parts of the compound of the formula (50), (108), (127) or (151) in a tumbler. The chips treated in this manner are then melted in a boiler heated at 300° C, from which the atmospheric oxygen has been displaced with superheated steam, and the melt is stirred for ½ hour, then expressed through a spinneret under a nitrogen pressure of 5 atmospheres (gauge), and the resulting, cooled filament is wound on a spinning top, whereby it is at the same time stretched.

The addition of the above-mentioned compounds substantially inhibits the degradation of the macromolecules caused during the exposure in the fadeometer and determined by measuring the relative viscosity in concentrated sulphuric acid. Other compounds of the Table behave similarly.

EXAMPLE 13

0.3 Gram of the compound of the formula (25) is dissolved in 10 g of pure olive oil. The compound dissolves rapidly and without heating. A 50µ-thick layer of this solution absorbs ultraviolet light up to 340 mµ.

In the same manner other fatty oils and creams, or emulsions used for cosmetic purposes may be used for dissolving the above compound and others, for example the compound (50), (81), (98), (121) or (182).

EXAMPLE 14

12 Grams of polyacrylonitrile are sprinkled with stirring into 88 g of dimethylformamide until all has dissolved, and then 0.1 g of the compound of, for example, formula (79) is added which dissolves immediately. The viscous mass is then applied to a cleaned pane of glass and spread out with a film drawing rod. The coated pane is then dried for 20 minutes in a vacuum drying cabinet at 120° C and under a vacuum of 150mm Hg. A foil about 0.05mm thick is obtained which is easy to detach from the glass support. The foil obtained in this manner is completely colourless and absorbs ultraviolet light up to a wavelength of 350mµ almost completely, while a foil not containing the absorber of the formula (79) passes at least 80% of the ultraviolet light. Incidentally, the compounds mentioned in connection with polystyrene are also suitable for incorporation with polyacrylonitrile.

What is claimed is:

1. A composition of matter substantially consisting of an organic material that can be damaged by ultraviolet rays, having incorporated therein an ultraviolet absorbing agent in a proportion sufficient to protect said material against the influence of ultraviolet rays, said ultraviolet absorbing agent being represented by an asymmetrical oxalic acid diarylamide of the formula

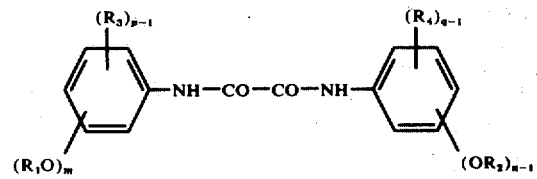

in which $R_1$ and $R_2$ each stands for a member selected from the group consisting of an alkyl group with 1 to 18 carbon atoms which may be substituted by a member selected from the group consisting of chlorine, a hydroxyl group, an alkoxy group with 1 to 4 carbon atoms, a carboxyl group, a nitrile group, a carboxylic acid amide group and a carboxylic acid alkyl ester groups with 1 to 12 carbon atoms, an alkenyl group with 3 to 4 carbon atoms, a benzyl group which may be substituted by chlorine atoms or alkyl groups, an aliphatic acyl group containing up to 18 carbon atoms and a benzoyl group which may be substituted by chlorine or an alkyl group with 1 to 4 carbon atoms; $R_3$ and $R_4$ each stands for a member selected from the group consisting of an alkyl group with 1 to 12 carbon atoms, a halogen atom, halogenalkyl group, a sulphonic acid group, a phenyl group and a phenylalkyl group whose alkyl residue contains 1 to 4 carbon atoms, or in each case two-ortho-positioned residues R₃ and/or R₄ together form a fused-on six-membered aromatic carbon ring, and m and n = 1 or 2 and p and q = 1, 2 or 3, each of the two ring systems containing apart from the bond via the —NH—group at most three substituents and the sum m+(m−1) = 1 or 2, and in other respects the substituents R₁O—, R₂O—, R₃ and R₄ being so constituted as to kind, number or positions that the molecule is asymmetrical.

2. A composition of matter as claimed in claim 1, containing as ultraviolet absorbing agent an asymmetrical oxalic acid diarylamide of the formula

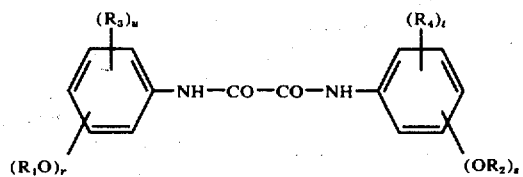

in which R₁ and R₂ each stands for a member selected from the group consisting of an alkyl group with 1 to 18 carbon atoms (which may be substituted by a member selected from the group consisting of chlorine, hydroxyl, an alkoxy group with 1 to 4 carbon atoms, a carboxyl group, a carboxylic acid amide group and a carboxylic acid alkyl ester group containing 1 to 12 carbon atoms), an alkenyl group with 3 to 4 carbon atoms, a benzyl group which may be substituted by chlorine or methyl groups, an aliphatic acyl group with up to 18 carbon atoms, and a benzoyl group which may be substituted by chlorine or an alkyl group with 1 to 4 carbon atoms; R₃ and R₄ each stands for a member selected from the group consisting of an alkyl group with 1 to 12 carbon atoms, a halogen atom, a halogenalkyl group, a sulphonic acid group, a phenyl group and a phenylalkyl group whose alkyl residue contains 1 to 4 carbon atoms or in each case two ortho-positioned residues R₃ and/or R₄ together form a fused-on six-membered aromatic carbon ring; r, s, t and u = 0 or 1, and the sum (r+s) = 1 or 2, and in other respects the substituents R₁O—, R₂O—, R₃ and R₄ being so constituted as to kind, number or positions that the molecule is asymmetrical.

3. A composition of matter as claimed in claim 1, containing as ultraviolet absorbing agent an asymmetrical oxalic acid diarylamide of the formula

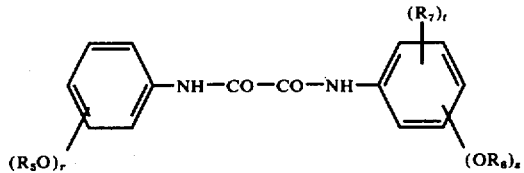

in which R₅ and R₆ stands for a member selected from the group consisting of an alkyl group with 1 to 18 carbon atoms which may be substituted by a member selected from the group consisting of chlorine, a hydroxyl group and an alkoxy group containing 1 to 4 carbon atoms, an alkyl group, a benzyl group which may be substituted by chlorine or methyl groups, a carbomethoxyalkyl group, a carbethoxyalkyl group, said alkyl groups containing 1 to 6 carbon atoms, an aliphatic acyl group with 1 to 12 carbon atoms and a benzoyl group which may contain chlorine or an alkyl group with 1 to 4 carbon atoms; R₇ represents an alkyl group with 1 to 18 carbon atoms, a chlorine atom or a phenyl group, r, s and t = 0 or 1 and the sum (r+s) = 1 or 2, and in other respects the substituents R₅O—, R₆O— and R₇ are so constituted as to kind, number and positions that the molecule is asymmetrical.

4. A composition of matter as claimed in claim 1, containing as ultraviolet absorbing agent an asymmetrical oxalic acid diarylamide of the formula

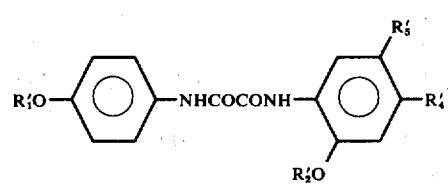

wherein
R₁' is methyl or ethyl,
R₂' is alkyl with 1 to 18 carbon atoms, 3-chloropropyl, 2-chloroethyl, allyl, benzyl, alkanoyl with 2 to 12 carbon atoms, acrylyl, benzoyl, p-chlorobenzoyl, p-tert-butylbenzoyl, 5-cyano-3-oxapentyl, carboethoxymethyl, carboxymethyl, carbododecyloxymethyl, butylcarbamyl or carbaniloylmethyl,
R₄' is hydrogen, methyl, methoxy, phenyl or α, α-dimethylbenzyl, and
R₅' is hydrogen, alkyl with 1 to 8 carbon atoms, chlorine or phenyl, and with the further proviso that when R₂' is methyl or ethyl, R₄' and R₅' cannot both be hydrogen at the same time.

5. A composition of matter as claimed in claim 1, containing as ultraviolet absorbing agent an asymmetrical oxalic acid diarylamide of the formula

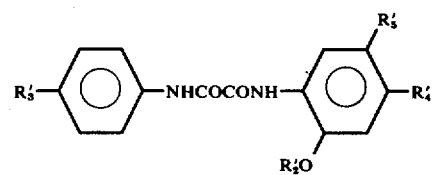

wherein
R₃' is hydrogen, chlorine or methyl,
R₂' is alkyl with 1 to 18 carbon atoms, 3-chloropropyl, carboethoxymethyl, benzyl or acetyl,
R₄' is hydrogen, methoxy or phenyl, and
R₅' is hydrogen or tert-butyl, and with the further proviso that when R₂' is methyl or ethyl, R₄' and R₅' cannot both be hydrogen at the same time.

6. A composition of matter as claimed in claim 1, containing as ultraviolet absorbing agent an asymmetrical oxalic acid diarylamide of the formula

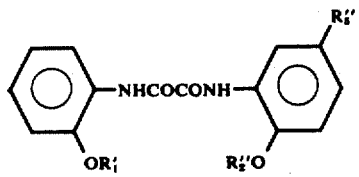

wherein
 R′₁ is methyl or ethyl,
 R₂″ is alkyl of 1 to 8 carbon atoms, 3-chloropropyl, benzyl, carboethoxymethyl or acetyl, and
 R₅″ is hydrogen, chlorine or tert-butyl, and with the further proviso that R₅″ cannot be hydrogen when R₂″ is methyl or ethyl.

7. A composition of matter as claimed in claim 1, containing as ultraviolet absorbing agent an asymmetrical oxalic acid diarylamide of the formula

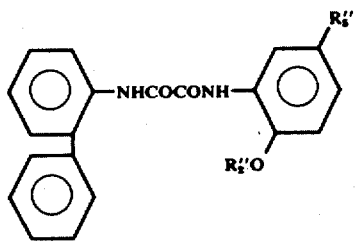

wherein
 R₂″ is alkyl with 1 to 8 carbon atoms, 3-chloropropyl, carboethoxymethyl or acetyl, and
 R₅″ is hydrogen or tert-butyl.

8. A composition of matter as claimed in claim 1, containing as ultraviolet absorbing agent an asymmetrical oxalic acid diarylamide of the formula

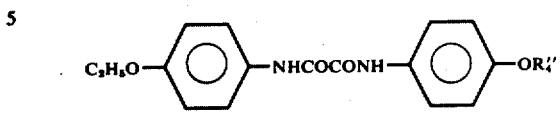

wherein
 R₄″ is alkyl of 4 to 12 carbon atoms, allyl, benzyl, octanoyl, benzoyl or p-tert-butylbenzoyl or butylcarbamyl.

9. A composition of matter as claimed in claim 1, containing as ultraviolet absorbing agent an asymmetrical oxalic acid diarylamide compound selected from the group consisting of 2′,4′-dimethyl-4″-methoxyoxanilide, 3′,5′-dimethyl-4″-methoxyoxanilide, 3,5′-dichloro-4″-methoxyoxanilide 3′-chloro-5′-trifluoromethyl-4″-methoxyoxanilide, 3′,5′-ditrifluoromethyl-4″-methoxyoxanilide, N-(4-methoxyphenyl)-N′-(α-naphthyl)oxamide, 2′-methyl-6′-chloro-4″-methoxyoxanilide, 4′-bromo-4″-methoxyoxanilide, 2′,2″,5′-triethoxyoxanilide and 4′-cyano-2″-ethoxyoxanilide.

10. A composition of matter as claimed in claim 1, wherein the amount of asymmetrical oxalic acid diarylamide ultraviolet absorbing agent therein defined is from 0.01 to 10% by weight of the composition.

11. A composition of matter as claimed in claim 10, wherein the amount of asymmetrical oxalic acid diarylamide ultraviolet absorbing agent is from 0.2 to 2.0% by weight.

12. A composition as claimed in claim 1, wherein said organic material consists acetyl cellulose, poly(vinyl chloride), polyolefine, unsaturated polyesters, polystyrene, nitrocellulose, polymethanes, polyamides, unsaturated fatty oils, or polyacrylonitrile.

* * * * *